US006013530A

United States Patent [19]
Tawara

[11] Patent Number: 6,013,530

[45] Date of Patent: Jan. 11, 2000

[54] PROCESS FOR DETERMINATION OF SULFUR CONTENT

[76] Inventor: Kinya Tawara, 3-9-9 Maeji, Urawa, Saitama, Japan

[21] Appl. No.: 08/871,894

[22] Filed: Jun. 9, 1997

Related U.S. Application Data

[63] Continuation of application No. 08/551,039, Oct. 30, 1995, abandoned.

[30] Foreign Application Priority Data

Oct. 31, 1994 [JP] Japan .................................... 6-290483

[51] Int. Cl.[7] .................................................... G01N 31/12

[52] U.S. Cl. ............................. 436/123; 422/83; 436/119

[58] Field of Search .................................... 436/123, 119, 436/84; 422/83, 94, 186.04

[56] References Cited

U.S. PATENT DOCUMENTS

| | | | |
|---|---|---|---|
| 3,602,711 | 8/1971 | Arora | 250/43.5 |
| 3,838,969 | 10/1974 | Dugan | 436/119 X |
| 3,853,474 | 12/1974 | Ausrtin | 436/119 X |
| 4,172,705 | 10/1979 | Castro et al. | 436/119 |
| 4,406,872 | 9/1983 | Kapner et al. | 423/461 |
| 4,409,069 | 10/1983 | Luft | 204/1 T |
| 4,428,921 | 1/1984 | Seike | 423/569 |
| 4,732,886 | 3/1988 | Tomino et al. | 502/314 |
| 4,740,473 | 4/1988 | Tomlin | 436/79 |
| 4,749,656 | 6/1988 | Ellerbe | 436/83 |
| 4,828,800 | 5/1989 | Castleman | 422/83 |
| 5,030,774 | 7/1991 | Oswald et al. | 568/882 |
| 5,116,759 | 5/1992 | Klainer et al. | 435/288 |
| 5,141,715 | 8/1992 | Sackinger et al. | 422/186.04 |
| 5,292,702 | 3/1994 | Seamans et al. | 502/219 |
| 5,424,217 | 6/1995 | Benner et al. | 436/123 |

OTHER PUBLICATIONS

Harry V. Drushel, "Trace sulfur Determination in Petroleum Fractions", Analytical Chemistry, vol. 50, No. 1, 76–81, Jan. 19, 1978.

ASTM D 4045–87, "Experminental Data and Reference for Experiments", an American National Standard, pp. 208–211, May 1987.

*Primary Examiner*—Jill Warden

*Attorney, Agent, or Firm*—Armstrong, Westerman, Hattori, McLeland & Naughton

[57] ABSTRACT

In a sulfur determining process, comprising a hydrocracking step of a sample in a ceramic reactor and darkness measuring step of lead acetate soaked tape by reaction of produced $H_2S$, an improvement is made. The improvement comprises at least one of procedure selected from the group consisting of introduction of $CO_2$ in the ceramic reactor, using an inverted AC current from stabilized DC current as an electric supply for the darkness measuring step, covering a box containing the darkness measuring sensor and a sensor circuit with a heat insulating material, A/D converting a differential output and making moving averages for making a noiseless record, and charging the differential output to a condenser through an electric resistance for making a noiseless record. Sulfur content is measured from a record of improved output. According to the improvements, an economic conventional ceramic reactor becomes available, and limit of sulfur determination of 25 ppb is improved to 2 ppb in the best case.

22 Claims, No Drawings

PROCESS FOR DETERMINATION OF SULFUR CONTENT

This application is a continuation of application Ser. No. 08/551,039, filed Oct. 30, 1995, now abandoned.

BACKGROUND OF THE INVENTION

This invention relates to an improvement of a process for determination of sulfur content.

Determination of trace sulfur is important for petroleum industries or chemical industries, for example, it is important for gasoline reforming or hydrogenation. By fine control, more useful performances of catalyst can be obtain or longer catalyst lives can be gain. For example, Ru catalyst has been found to be more useful for steam reforming to prevent carbon deposit in lower steam/carbon ratio than Ni catalyst. It was, however, very difficult to use it successfully. Because the life of catalyst having small quantity of Ru, is shorter than that of catalysts having large quantity of Ni. To realize industrial Ru catalyst fine control of feed becomes important.

There have been used several methods to determine a small quantity (for example 0.1 to 1 wt ppm) of sulfur. They are not, however, sufficient to determine smaller quantity of sulfur than 0.1 wt ppm.

ASTM D 4045-87 provides a method to analyze sulfur. According to this method Sulfur Analyzer Model 856/825R-d/1003 is manufactured by Houston Atlas Inc. The analyzer has high sensitivity and stability for determination of sulfur content in light petroleum fraction, and is used in USA and all over the world.

According to this method, at first stream of sample and hydrogen are injected steadily into a heated (1,100 to 1,400° C.) ceramic tube and $H_2S$ containing produced gas is introduced in a window-cell in which a lead acetate soaked tape is set. The tape becomes dark gradually. Darkness of the tape is measured using photo sensor continuously, and differential output (rate of change of darkness) is drawn on a recorder. Sulfur content is determined from the height of the record. It is very important to avoid losses of $H_2S$ due to adsorption in the path from heated reaction zone to the window-cell.

The present inventor has found some subjects that should be improved in this Analyzer as follows:

(1) Conventional alumina tube shall be used for hydrocracking ceramic tube. It is thermal resistant and not expensive. It contains small quantity of Fe, Na. Ca, and Mg as impurities. The present inventor has found that produced $H_2S$ is adsorbed on the impurities, as the result determined sulfur value becomes lower or does not appear at all. From that reason specially manufactured pure alumina tube is provided. This tube can be used in determination of larger quantity than 25 ppb level of sulfur with no problem. The tube is, however, expensive and is not strong thermally or mechanically. To improve this point addition of impurity becomes necessary, but added impurity causes adsorption. Impurity content is reduced in this specially manufactured pure alumina tube, but it still contains smaller quantity of impurity, therefore it is available for determination of larger quantity of sulfur than 25 ppb, but is not sufficient for detection of smaller quantity than 25 ppb. Especially in determination of 10 ppb level of sulfur content, large error was found as shown in comparative example 5. Therefore, this tube is requested an additional improvement for low level sulfur determination.

(2) The determination is disturbed by carbon deposit produced in the hydrocracking tube. $H_2S$ is adsorbed on the carbon deposit, especially in determination of kerosene. In that case carbon deposit shall be burn out, this procedure is complicated, because several steps to purge out $H_2$ and $O_2$ with $N_2$ in each step are necessary.

To reduce carbon deposit, limited quantity of air is introduced before hydrocracking reaction, hydrocarbon is burned before hydrocracking reaction. This pre burning (OXY HYDRO) procedure has been developed as a prior art. It is, however, not sufficient for detection of smaller quantity than 0.1 ppm. Especially in determination of 10 ppb level of sulfur content, large error was found as shown in comparative example 5 in using pure alumina tube for hydrocracking, and also larger error was found in using conventional silica alumina tube as shown in comparative example 4.

(3) It is announced that limit of detection is 20 to 40 ppb in light petroleum fraction like naphtha, and 30 to 40 ppb in heavy petroleum fraction like kerosene. This limit is, however, not sufficient for recent development of catalysts for petroleum refinery and chemical plants. Therefore ten times larger sensitivity is required. Moreover, high noise level of this analyzer makes difficult to detect small peak and to improve limit of detection.

SUMMARY OF THE INVENTION

The present inventor performed research to solve the $H_2S$ adsorption trouble on alumina containing trace quantity of impurity such as Fe, Na, Ca, and Mg. Then the present inventor has found a phenomenon that adsorbed $H_2S$ can be swept off by substitute adsorption of $CO_2$. Adsorption of $H_2S$ on the tube reduces effectively by adding $CO_2$ in hydrogen stream. At the same time by reaction of $CO_2$ with carbon deposit, carbon deposit decreases. As the result, determination is carried out successfully.

Moreover when detection of sulfur is carried out by measuring darkness caused by formation of lead sulfate using differential output of optical sensor circuit, at least one of following improvements has been found to be useful to realize a more sensitive determination:

(1) An electric supply for the optical sensor is improved using inverted AC current from stabilized DC current that converted from conventional AC supply and charged in a battery or a condenser.

(2) Temperature in a box containing the photo sensor and the measuring sensor circuit is stabilized by covering the box with heat insulating material to avoid a property change of electronic parts.

(3) Differential output from the optical sensor circuit is A/D converted at 0.1 to 5 second interval, using these 10 to 50 values moving averages are made, the average values are D/A converted, recorded finally and from height of the record sulfur is determined.

(4) Differential output from the optical sensor circuit is charged to a 100 to 300,000 $\mu$F condenser through an 1 to 100 k$\Omega$ electric resistance, potential of the condenser is recorded, and from height of the record sulfur is determined.

Accordingly, the present invention provides in one aspect an improvement. That is; In a process for determining sulfur content in which sulfur containing sample is burned previously if necessary (OXY HYDRO PROCEDURE), hydrocracked in next reactor, and sulfur is determined by measuring concentration of $H_2S$ in produced gas, an improvement was made comprising introduction of $CO_2$ in stabilizing period and sample charging period into the pre burning reactor or into the hydrocracking reactor or into both reactors.

The present invention provides in another aspect an improvement. That is; In a process for determining sulfur content in which sulfur containing sample is burned previously if necessary (OXY HYDRO PROCEDURE), hydrocracked in next reactor, produced $H_2S$ containing gas is introduced into a lead acetate soaked tape set window-cell, the tape becomes dark gradually, measuring differential output of photo sensor circuit, and sulfur is determined, an improvement was made which comprises at least one of procedure selected from the group consisting of ① introducing $CO_2$ in stabilizing period and sample charging period into the pre burning reactor or into the hydrocracking reactor or into both reactors, ② improving an electric supply for the optical sensor using inverted AC current from stabilized DC current which converted from conventional AC supply and charged in a battery or a condenser, ③ covering a box containing the photo sensor and the measuring sensor circuit with heat insulating material to avoid a property change of electronic parts, ④ A/D converting at 0.1 to 5 second interval the differential output from the optical sensor circuit, making moving averages using these 10 to 50 values, D/A converting and recording the moving averages, and determining sulfur content from height of the record, and ⑤ charging the differential output from the optical sensor circuit to a 100 to 300,000 $\mu$F condenser through an 1 to 100 k$\Omega$ electric resistance, recording potential of the condenser, and determining sulfur content from height of the record.

DETAILED DESCRIPTION OF THE INVENTION

Any kinds of gaseous or liquid sample can be detected in the present invention. For example, $N_2$, $H_2$, $H_2O$, hydrocarbons, oxygen containing organic compounds, nitrogen containing organic compounds and halogen containing organic compounds are available. These hydrocarbons, oxygen containing organic compounds, nitrogen containing organic compounds, and halogen containing organic compounds, are not limited to specified compounds, and many compounds are available. For example, hydrocarbons, natural gas, light petroleum fractions such as naphtha, other petroleum fractions heavier than kerosene and many kinds of chemicals are available.

Any types of sulfur are available, for example, sulfur itself, sulfur in linear compounds or sulfur in ring compounds are available.

Content of sulfur is not limited. Small quantity such as below 10 ppb or large quantity such as above 100 ppm is available. It is a big advantage in the present invention that smaller quantity than 40 ppb of sulfur can be detected exactly.

In the present invention, sulfur compound is hydrocracked in the reaction tube, and sulfur in the compound converts to $H_2S$. The hydrocracking reaction proceeds by mixing the sulfur containing sample with hydrogen in heated tube. Mixing ratio of hydrogen with sample is not limited, but suitable ratio is available. One preferred ratio is 10 thousand to 200 thousand times of volume of hydrogen gas per one volume of sample measured as liquid, preferable ratio is 60 thousand to 150 thousand times.

Reaction temperature of hydrocracking can be selected according to reactivity of sample. 1,000 to 1,800° C. is usually used, and 1,100 to 1,500° C. is preferable.

As material for reaction tube, conventional alumina is preferable in the prevent invention. Silica, silica-alumina, zirconia, pure alumina or other ceramics are available too.

Reaction tube is used without packing materials usually, but can be used with packing materials. Shape of packing materials is not limited, particle, linear or stick shapes are available.

In the present invention, if necessary, sample is burned before hydrocracking reaction. This pre burning is useful to prevent carbon deposit for sample containing large quantity of carbon. Burning reaction is carried out by injecting sample and oxygen or oxygen containing gas to the pre burning reaction tube. As oxygen containing gas various oxygen containing gas are available, air is preferable.

Quantity of oxygen or oxygen containing gas can be selected to such an extent that formation of carbon deposit is prevented. 50 to 300% quantity of perfect combustion is used, 90 to 280% quantity of perfect combustion is preferable. If quantity of oxygen or oxygen containing gas is excess, hydrogen is consumed. Therefore production of $H_2S$ is disturbed and $SO_3$ is formed, which is difficult to convert to $H_2S$ and as a result determined sulfur quantity becomes smaller.

Pre burning temperature is not limited, about 500° C. is preferable. In the present invention, $CO_2$ is introduced into the hydrocracking tube. When pre burning tube is used, $CO_2$ is introduced into the one of tubes or into both tubes.

By introduction of $CO_2$, adsorption of $H_2S$ on the wall of tube or packed materials is avoided, and as the result, determination of sulfur can be carried out exactly.

Procedure to introduce $CO_2$ is not limited, any procedures are available, for example from the special inlet of the one of tubes or both tubes. $CO_2$ can be introduced as mixed gas with $H_2$, or with oxygen or oxygen containing gas.

Mixing ratio of $CO_2$ with $H_2$ is 5 to 70% volume of $CO_2$ per 100% volume of $H_2$, preferably 7 to 30% is available. Smaller ratio than these is not effective and larger ratio than these is not preferable for hydrocracking reaction.

The inventor surprisingly has found that in the pre burning procedure, adsorbed $H_2S$ on the wall of the tube is desorbed by small quantity of produced $CO_2$ from pre burning reactor, in that case measured quantity of $H_2S$ is higher than that of contained in the sample. In determination of small quantity of sulfur, error becomes large. For example, in a determination of a sample which had 8 ppb sulfur, 67 to 28 ppb value was shown. The inventor has found that these errors can be avoided by introducing $CO_2$ constantly before determination, and by attaining an equilibrium of adsorption on the wall.

In the present invention, it is preferable that the ratio of $CO_2/H_2$ does not change during determination. It is preferable to reduce $CO_2$ introduction quantity to compensate $CO_2$ quantity produced from pre burning reaction during determination.

Produced $H_2S$ can be measured by several methods. For example, it can be measured by introducing this gas to lead compound containing solution, and determining darkness of the solution. Instead of lead compound solution, lead acetate soaked tape is used in the ASTM D 4045-87 method. $H_2S$ can be also measured by accomplished instruments for example by mass spectrometer. In the method provided in ASTM D 4045-87, darkness of lead acetate soaked tape is measured and differential output of photo sensor circuit is recorded. When determination of smaller sulfur content than 40 ppb is needed, the output shall be magnified to ten times, but it is difficult because the output contains high noise level.

The present inventor performed research to solve this problem. As a result, the inventor has found that some kinds of noise decrease as follows;

(1) An electric supply for the optical sensor is improved using inverted AC current from stabilized DC current which converted from conventional AC supply and charged in a battery or a condenser.

(2) Temperature in a box containing the photo sensor and the measuring sensor circuit is stabilized by covering the box with heat insulating material to avoid a property change of electronic parts, (3) Differential output from the optical sensor circuit is A/D converted at 0.1 to 5 second interval, using these 10 to 50 values moving averages are made, the average value is D/A converted, recorded finally and from height of the record sulfur content is determined.

(4) Differential output from the optical sensor circuit is charged to a 100 to 300,000 $\mu$F condenser through an 1 to 100 k$\Omega$ electric resistance, potential of the condenser is recorded, and from height of the record sulfur content is determined.

In the present invention each noise decreasing method can be used alone or combined. Using these combined noise decreasing methods, limit of sulfur content determination becomes 1 to 2 ppb, without noise decreasing method, limit of determination is 30 to 50 ppb Next examples are the illustrations of the present invention, and are not meant to be limiting.

EXAMPLE 1

SULFUR ANALYZER 856/825R-d/1003 (manufactured by Houston Atlas Inc.) with conventional silica alumina hydrocracking tube was used. 10% of $CO_2$ mixed $H_2$ was introduced to the hydrocracking tube at a rate of 480 ml/m at 1,400° C., before determination for 8 hours. Keeping the same conditions, sample was introduced from micro syringe at 3.3 $\mu$l/m for 30 minutes. As 1st and 6th sample 1.0 $\mu$l/ml sulfur (n-butylsulfide) containing isooctane was used to approve determination, as 2nd to 5th sample hydrodesulfurized naphtha was used. By $CO_2$ effect, produced $H_2S$ was measured perfectly without adsorption on the wall of the reactor. Quantity of carbon deposited was small, and the same quantity of sulfur was determined in the 1st and 6th sample respectively. There was no determination loss after continuous six time's use.

EXAMPLE 2

SULFUR ANALYZER 856/825R-d/1003 with conventional silica alumina hydrocracking tube was used and pre burning tube was used. 73 ml/m of air was introduced into pre burning tube and 10% of $CO_2$ mixed $H_2$ was introduced to the hydrocracking tube at a rate of 209 ml/m at 1,300° C., in these state tubes were stabilized before determination for 8 hours. Keeping the same conditions, sample was introduced from a micro syringe at 3.3 $\mu$g/m for 30 minutes. As 1st and 6th sample 1.0 $\mu$g/ml sulfur (n-butylsulfide) containing isooctane was used to approve determination, as 2nd to 5th sample hydrodesulfurized kerosene was used. By $CO_2$ effect, produced $H_2S$ was measured perfectly without adsorption on the wall of the reactor. Quantity of carbon deposit was small, and the same quantity of sulfur was determined in the 1st and 6th sample respectively. There was no determination loss after continuous six time's use.

EXAMPLE 3

20.7% of $CO_2$ mixed air was introduced in the pre burning tube, and 190 ml/m of $H_2$ is introduced to the hydrocracking tube. The other conditions were the same as example 2, and the same determinations as example 2 were carried out. By $CO_2$ effect, Produced $H_2S$ was measured perfectly without adsorption on the wall of the reactor. Quantity of carbon deposit was small, and same quantity of sulfur was determined in the 1st and 6th sample respectively. There was no determination loss after continuous six time's use.

COMPARATIVE EXAMPLE 1

432 ml/m of pure $H_2$ was introduced into the hydrocracking tube. The other conditions were the same as example 1, and the same determinations as example 1 were carried out. Almost all of $H_2S$ produced in the hydrocracking tube was adsorbed and could not be detected. After that, to watch adsorption trend on this tube, 10 $\mu$g/ml sulfur (n-butylsulfide)containing isooctane was introduced from a micro syringe five times, in each time the sample was introduced at 3.3 $\mu$l/m rate for 30 minutes continuously. Determined each sulfur ratio per each charge was 0.3%, 2.0%, 3.8%, 4.4% and 7.2% respectively. Increasing trend was watched but it was surprising that so large quantity of $H_2S$ was adsorbed. The conventional silica-alumina tube used here, contained CaO, MgO, $Na_2O$, and $Fe2O_3$ as impurities, and total quantity was 0.5 wt %. Produced $H_2S$ was adsorbed on the impurity.

COMPARATIVE EXAMPLE 2

Instead of conventional silica alumina tube, pure alumina tube was used as the hydrocracking reactor, and as 2nd to 5th sample, hydrodesulfurized kerosene was used instead of hydrodesulfurized naphtha. The other conditions were the same as comparative example 1, and the same determinations as comparative example 1 were carried out. From the 1st determination, produced $H_2S$ was measured almost perfectly without adsorption on the wall of the reactor. Because large quantity of carbon deposit on the wall of the reactor formed, at 6th determination some part of $H_2S$ was adsorbed on the carbon deposit therefore, 94% sulfur determined compared to that of 1st determination. To remove carbon deposit, temperature was dropped to 900° C., residual $H_2$ was purged with $N_2$, carbon deposit was burned out by passing air, and after burning residual air was purged with $N_2$. After regeneration the same value of sulfur as that of 1st determination was determined.

EXAMPLE 4

SULFUR ANALYZER 856/825R-d/1003 with conventional silica alumina hydrocracking tube was used. 10% of $CO_2$ mixed $H_2$ was introduced to the hydrocracking tube at a rate of 300 ml/m at 1,400° C. before determination for 8 hours. Keeping these conditions, samples (32 ppb and 14 ppb of sulfur containing hydrodesulfurized kerosene) were introduced from a micro syringe at 3.3 $\mu$l/m for 30 minutes. The original electric supply for the optical sensor circuit was changed by hand-craft with an inverted AC current (50 Hz 115v) from stabilized DC current which was converted from conventional AC supply and charged in a battery. Temperature in the box containing photo sensor and measuring sensor circuit was stabilized by covering with heat insulating material (3 mm flame-proof urethane foam rubber) inside of the box to avoid a rapid property change of electronic parts. Differential output was A/D converted at 5 second interval, using 50 values moving averages were made, the average value was D/A converted, and recorded in a sensitive pen recorder. As the result, noise decreased and determination limit of 30 ppb was improved to 7 ppb.

EXAMPLE 5

Instead of moving average procedure, differential output was connected to a condenser (9,400 μF) through an electric resistance (10 kΩ) and potential of the condenser was recorded. Other conditions were the same as example 4 and the same determinations as example 4 were carried out. The same preferable results as example 4 were found.

EXAMPLE 6

Instead of 9,400 μF condenser 220,000 μF condenser was used, and recorder attenuater was set as 8 times sensitive. The other conditions were the same as example 5 and the same determinations as example 5 were carried out. As the result, noise decreased and determination limit of 30 ppb was improved to 2 ppb.

EXAMPLE 7

Instead of conventional silica alumina tube, pure alumina tube was used as the hydrocracking reactor. Pure $H_2$ was introduced to the tube at a rate of 300 ml/m at 1,400° C., before determination for 8 hours. The other conditions were the same as example 5, and the same determinations as example 5 were carried out. The same preferable results as example 5 were found.

COMPARATIVE EXAMPLE 3

Inverted AC supply and condenser (9,400 μF) were not used. Instead of samples (32 ppb and 14 ppb of sulfur containing hydrodesulfurized kerosene) 64 ppb and 172 ppb sulfur containing kerosene were used. Other conditions were the same as example 7, and the same determinations as example 7 were carried out. As the result, noise did not decrease and determination limit was 30 ppb.

EXAMPLE 8

SULFUR ANALYZER 856/825R-d/1003 with conventional silica alumina hydrocracking tube and pre burning tube were used. 73 ml/m of air was introduced to the pre burning tube. Moreover, 190 ml/m of pure $H_2$ and 19 ml/m of $CO_2$ were introduced to the hydrocracking tube. Under this state at 1,300° C., tubes were stabilized before determination for 8 hours. Keeping the same conditions, 32 ppb sulfur (n-Buthylsulfide) containing isooctane was introduced from a micro syringe at 3.3 μl/m for 30 minutes. From the first, exact sulfur value was determined.

COMPARATIVE EXAMPLE 4

$CO_2$ was not used. Other conditions were the same as example 8 and the same determinations as example 8 were carried out. At the first determination, more than 1,000 ppb of value was shown. The present inventor found that during stabilization before determination, impurity (for example $SO_4$) containing in the hydrocracking tube was reduced to $H_2S$ gradually by hydrogen and adsorbed in the hydrocracking reactor. Adsorbed $H_2S$ is desorbed by $CO_2$ produced during pre burning reaction and as the result, large error was shown. After this test, next three continuous determinations showed 120 ppb, 84 ppb and 56 ppb respectively, but the values did not reach to the exact value yet.

COMPARATIVE EXAMPLE 5

Instead of conventional silica alumina tube, pure alumina tube was used, and instead of 32 ppb sulfur (n-Buthylsulfide) containing isooctane, 8 ppb of sulfur containing hydrodesulfurized kerosene was used. Other conditions were the same as comparative example 4 and the same determinations as comparative example 4 were carried out. From the 1st to the 6th continuous determination, the values 67 ppb, 56 ppb, 42 ppb, 31 ppb, 28 ppb and 25 ppb respectively were shown, but the values did not reach to the exact value yet. After tests, the hydrocracking tube was changed to new one and 19 ml/m $CO_2$ was introduced into the hydrocracking tube additionally. From the first determination, exact sulfur value was shown.

What is claimed is:

1. A process to determine sulfur content of a sulfur containing sample comprising a method selected from the group consisting of (a) hydrocracking a sample with $H_2$ in a hydrocracking ceramic reactor, introducing produced $H_2S$ containing gas into a window-cell where a lead compound soaked tape is set, measuring darkness of said tape using a photo sensor, measuring value of differential output from a photo sensor circuit for determining sulfur content, and (b) burning a sample in a preburning ceramic reactor, hydrocracking the preburned sample with $H_2$ in a hydrocracking ceramic reactor, introducing produced $H_2S$ containing gas into a window-cell where a lead compound soaked tape is set, measuring darkness of said tape using a photo sensor, measuring value of differential output from a photo sensor circuit for determining sulfur content, the improvement comprising a procedure selected from the group consisting of (1) continuously introducing $CO_2$ during stabilizing period and sample charging period into at least one of said reactor selected from the group consisting of said preburning ceramic reactor and said hydrocracking ceramic reactor, wherein $CO_2/H_2$ volume ratio is 0.07 to 0.3, (2) using inverted AC current from stabilized DC current which has been converted from conventional AC supply and charged in a battery or a condenser as an electric supply for said photo sensor, (3) covering a box which contains said photo sensor and said measuring sensor circuit with heat insulating material, (4) A/D converting at 0.1 to 5 second interval said differential output from said photo sensor circuit, making moving averages using these 10 to 50 values, D/A converting and recording said moving averages, and determining sulfur content from height of said record, and (5) charging said differential output from said photo sensor circuit to a 100 to 300,00 μF condensor through an 1 to 100 kΩ electric resistance, recording potential of said condenser, and determining sulfur content from height of said record.

2. A process to determine sulfur content in a sulfur containing sample, the process comprising the steps of:

(a) introducing carbon dioxide into said hydrocracking ceramic reactor;

(b) introducing said sample and hydrogen into said hydrocracking ceramic reactor to react said sample with hydrogen in said hydrocracking ceramic reactor, whereby decomposing sulfur in said sample into $H_2S$ and producing $H_2S$ containing gas; and (c) introducing said $H_2S$ containing gas into a measuring device to determine the sulfur content of said sample.

3. The process to determine sulfur content claimed in claim 2, wherein said carbon dioxide is introduced at a constant amount.

4. The process to determine sulfur content claimed in claim 2, wherein said carbon dioxide is introduced from before the time when said sample is introduced.

5. The process to determine sulfur content claimed in claim 2, wherein said carbon dioxide is introduced at a constant amount from before and through the time period when said sample is introduced.

6. The process to determine sulfur content claimed in claim 2, wherein said sample is burned in a preburning ceramic reactor before being introduced into said hydrocracking ceramic reactor.

7. The process to determine sulfur content claimed in claim 6, wherein carbon dioxide introduced into said hydrocracking ceramic reactor is first introduced into said preburning ceramic reactor and then introduced into said hydrocracking ceramic reactor through said preburning ceramic reactor.

8. The process to determine sulfur content claimed in claim 2, wherein said step of introducing said $H_2S$ containing gas further comprises:

(1) introducing said $H_2S$ containing gas to contact a lead compound soaked tape, (2) measuring darkness of said tape using photo sensor, (3) determining sulfur content by measuring value of differential output from a photo sensor circuit.

9. The process to determine sulfur content claimed in claim 8, wherein said photo sensor is supplied with inverted AC current from stabilized DC current which has been converted from conventional AC supply and which has been charged in a battery or condenser.

10. The process to determine sulfur content claimed in claim 8, wherein a box containing said photo sensor and said photo sensor circuit is covered with heat insulating material.

11. The process to determine sulfur content claimed in claim 8, said step of determining sulfur content further comprises:

(i) A/D converting said differential output from said photo sensor circuit at 0.1–5 second interval to obtain digital values;

(ii) making moving averages of 10–50 of said digital values;

(iii) D/A converting and recording said moving averages (iv) determining sulfur content from said recorded moving average.

12. The process to determine sulfur content claimed in claim 8, wherein differential output from said photo sensor circuit is charged to a 100–300,000 μF condenser through an 1–100 K ohm electric resistance, recording potential of said condenser.

13. The process to determine sulfur content claimed in claim 12, wherein said condenser is 10,000–220,000 μF.

14. The process to determine sulfur content claimed in claim 2, wherein $CO_2/H_2$ volume ratio is 0.07–0.3.

15. The process to determine sulfur content claimed in claim 6, wherein said step of determining sulfur content comprising:

(1) introducing said $H_2S$ containing gas to contact with a lead compound soaked tape, (2) measuring darkness of said tape using photo sensor, (3) measuring value of differential output from a photo sensor circuit for determining sulfur content.

16. The process to determined sulfur content claimed in claim 15, wherein inverted AC current from stabilized DC current which has been converted from conventional AC supply and which has been charged in a battery or condenser as an electric supply for said photo sensor.

17. The process to determine sulfur content claimed in claim 15, wherein a box containing said photo sensor and said photo sensor circuit is covered with heat insulating material.

18. The process to determined sulfur content claimed in claim 15, wherein differential output from said photo sensor circuit is A/D converted at 0.1–5 second interval making moving averages, and said moving averages of 10–50 is used in D/A conversion.

19. The process to determined sulfur content claimed in claim 15, wherein differential output from said photo sensor circuit is charged to 100–300,000 μF condenser through an 1–100 K ohm electric resistance, recording potential of said condenser.

20. A process to determine sulfur content in a sulfur containing sample, the process comprising the steps of:

(a) introducing said sample and hydrogen into said hydrocracking ceramic reactor to react said sample with hydrogen in said hydrocracking ceramic reactor so as to decompose sulfur contained in said sample in $H_2S$ to produce $H_2S$ containing gas;

(b) introducing produced $H_2S$ containing gas into a lead compound soaked tape set (c) measuring darkness of said tape using photo sensor, said photo sensor having inverted AC current from stabilized DC current which has been converted from conventional AC supply and charged in a battery or a condenser as an electric supply for said photo sensor; and (d) determining sulfur content by measuring value of differential output from a photo sensor circuit.

21. A process to determine sulfur content in a sulfur containing sample, the process comprising the steps of:

(a) introducing said sample and hydrogen into said hydrocracking ceramic reactor to react said sample with hydrogen in said hydrocracking ceramic reactor so as to decompose sulfur contained in said sample into $H_2S$ to produce $H_2S$ containing gas;

(b) introducing produced $H_2S$ containing gas into a lead compound soaked tape set window-cell;

(c) measuring darkness of said tape using a photo sensor;

(d) A/D converting at 0.1 to 5 second interval said differential output from said photo sensor circuit;

(e) making moving averages using these 10 to 50 values;

(f) D/A converting and recording said moving averages; and (g) determining sulfur content from height of said recorded moving averages.

22. A process to determine sulfur content in a sulfur containing sample, the process comprising the steps of:

(a) introducing said sample and hydrogen into said hydrocracking ceramic reactor to react said sample with hydrogen in said hydrocracking ceramic reactor so as to decompose sulfur contained in said sample into $H_2S$ to produce $H_2S$ containing gas;

(b) introducing produced $H_2S$ containing gas into a lead compound soaked tape set window-cell;

(c) measuring darkness of said tape using a photo sensor;

(d) charging said differential output from said photo sensor circuit to a 100–300,000 μF condenser through an 1–100 K ohm electric resistance;

(e) recording potential of said condenser; and (f) determining sulfur content from said recorded potential.

* * * * *

UNITED STATES PATENT AND TRADEMARK OFFICE

CERTIFICATE OF CORRECTION

PATENT NO. : 6,013,530
DATED : January 11, 2000
INVENTOR(S) : Kinya Tawara

It is certified that error appears in the above-identified patent and that said Letters Patent is hereby corrected as shown below:

Column 1,
Line 31, change "fraction" to -- fractions --.
Line 51 and 52, change "as the result" to -- as a result --.

Column 2,
Line 36, change "As the result" to -- As a result --.

Column 3,
Lines 14-27, change numbers "①-⑤" where they appear, to -- (1) - (5) --.

Column 4,
Line 18, change "280%" to -- 230% --.
Line 29, change "as the result" to -- as a result --.

Column 5,
Line 38, change "1.0μl/ml" to -- 1.0μg/ml --.
Line 55, change "3.3μg/ml" to -- 3.3μl/ml --.
Line 66, change "As the result" to -- As a result --.

Column 7,
Lines 14 and 15, change "As the result" to -- As a result --.
Line 59, change "as the result" to -- as a result --.

UNITED STATES PATENT AND TRADEMARK OFFICE
CERTIFICATE OF CORRECTION

PATENT NO. : 6,013,530
DATED : January 11, 2000
INVENTOR(S) : Kinya Tawara

It is certified that error appears in the above-identified patent and that said Letters Patent is hereby corrected as shown below:

Column 8,
Line 53, change "300,00 μF" to -- 300,000 μF --.

Column 10,
Line 19, change "in $H_2S$" to -- into $H_2S$ --.

Signed and Sealed this

Twenty-third Day of October, 2001

Attest:

Nicholas P. Godici

NICHOLAS P. GODICI

*Attesting Officer* *Acting Director of the United States Patent and Trademark Office*